US007325355B2

(12) United States Patent
Zeldis

(10) Patent No.: US 7,325,355 B2
(45) Date of Patent: Feb. 5, 2008

(54) METHODS FOR TREATMENT OF ATHEROSCLEROSIS USING 1,3-DIOXO-2-(2,6-DIOXOPIPERIDIN-3-YL)-4-AMINOISOINDOLINE

(75) Inventor: Jerome B. Zeldis, Princetone, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 11/216,950

(22) Filed: Aug. 30, 2005

(65) Prior Publication Data

US 2006/0004054 A1    Jan. 5, 2006

Related U.S. Application Data

(62) Division of application No. 09/734,460, filed on Dec. 11, 2000, now Pat. No. 7,182,953.

(60) Provisional application No. 60/170,820, filed on Dec. 15, 1999.

(51) Int. Cl.
*A61F 2/02* (2006.01)

(52) U.S. Cl. .......................................................... 42/423

(58) Field of Classification Search .................... None
See application file for complete search history.

(56) References Cited

FOREIGN PATENT DOCUMENTS

WO    WO9803502    *    1/1998

OTHER PUBLICATIONS

Definitions of "stereochemistry" and "enantiomer", Hawley's Condensed Chemical Dictionary, 14 th Edition, 2002.*

* cited by examiner

*Primary Examiner*—Carlos A. Azpuru
(74) *Attorney, Agent, or Firm*—Jones Day

(57) ABSTRACT

Methods and compositions for the prevention and treatment of all forms of atherosclerosis are described. Administration of compounds such as thalidomide, its analogs, hydrolysis products, metabolites, derivatives and precursors as well as additional compounds capable of inhibiting tumor necrosis factor $\alpha$(TNF-$\alpha$) are used in the invention.

Also disclosed is the coating of prosthetic devices, such as stents, with the compounds of the invention for the prevention and/or treatment of restenosis.

14 Claims, No Drawings

METHODS FOR TREATMENT OF ATHEROSCLEROSIS USING 1,3-DIOXO-2-(2,6-DIOXOPIPERIDIN-3-YL)-4-AMINOISOINDOLINE

CROSS-REFERENCE TO RELATED APPLICATION

This application is a divisional application of U.S. patent application Ser. No. 09/734,460, filed Dec. 11, 2000, now U.S. Pat. No. 7,182,953, which claims the benefit of U.S. provisional application No. 60/170,820, filed Dec. 15, 1999, the entireties of which are incorporated herein by reference.

1. INTRODUCTION

The invention is directed to methods and compositions for the prevention and treatment of all forms of atherosclerosis, including atherosclerosis found in the cardiovascular and renal systems. More particularly, the present invention relates to the prevention and or reduction of stenosis and restenosis by administration of compounds such as thalidomide, its analogs, hydrolysis products, metabolites, derivatives and precursors of thalidomide. Compounds which may be used in the methods and compositions of the invention typically are capable of inhibiting tumor necrosis factor α(TNF-α). In another embodiment, the present invention is directed to the coating of prosthetic devices with these compounds for use or implantation into a subject, preferably a human. Preferred prosthetic devices include, for example, stents coated with the compounds for the prevention and/or treatment of restenosis.

2. BACKGROUND OF THE INVENTION

In 1994, there were almost 1 million deaths due to vascular disease in the United States (twice as many as from cancer and 10 times as many as from accidents). Vascular disease may affect the brain, heart, kidneys, other vital organs as well as the extremities.

The most common and serious vascular disease is atherosclerosis. Atherosclerosis is characterized by patchy subintimal thickening (atheromas) of the medium-sized arteries such as the coronary arteries, mesenteric arteries, renal arteries and carotid arteries and the large arteries such as the aorta.

Development of atherosclerotic lesions involves proliferation of cellular constituents of the wall of blood vessels in response to chemical stimuli from platelets and monocytes derived from the blood. This proliferation of cells in the vessel wall can lead to narrowing of the lumen of the vessel. In addition, atherosclerotic plaques, the focal lesions of atherosclerosis, can be sites of thrombus or clot formation, hemorrhage, or ulceration leading to interruption of the blood supply of the organ supplied by the affected blood vessel e.g., thrombus formation over an atherosclerotic plaque in a coronary artery can occlude the vessel; depriving a portion of the heart of its blood supply and thus causing ischemic death or infarction of heart muscle. Atherosclerotic plaque consists of accumulated intracellular and extracellular lipids, smooth muscle cells, connective tissue, and glycosaminoglycans. The earliest detectable lesion of atherosclerosis is the fatty streak (consisting of lipid-laden foam cells, which are macrophages that have migrated as monocytes from the circulation into the subendothelial layer of the intima), which later evolves into the fibrous plaque (consisting of intimal smooth muscle cells surrounded by connective tissue and intracellular and extracellular lipids).

The death rate from coronary artery disease ("CAD") is significant, for example, the death rates among white men aged 25 to 34 is about 1/10,000; at age 55 to 64, it is nearly 1/100. This age relationship may be due to the time required for lesions to develop or to the duration of exposure to risk factors.

Atherosclerotic vessels are characterized by having reduced systolic expansion and abnormally rapid wave propagation. Arteriosclerotic arteries of hypertensive persons also have reduced elasticity, which is further reduced when atherosclerosis develops.

Two main hypotheses have been proposed to explain the pathogenesis of atherosclerosis: the lipid hypothesis and the chronic endothelial injury hypothesis.

The lipid hypothesis postulates that an elevation in plasma LDL levels results in penetration of LDL into the arterial wall, leading to lipid accumulation in smooth muscle cells and in macrophages (foam cells). LDL also augments smooth muscle cell hyperplasia and migration into the subintinal and intimal region in response to growth factors. LDL is modified or oxidized in this environment and is rendered more atherogenic.

The chronic endothelial injury hypothesis postulates that endothelial injury by various mechanisms produces loss of endothelium, adhesion of platelets to subendothelium, aggregation of platelets to subendothelium, aggregation of platelets, chemotaxis of monocytes and T-cell lymphocytes, and release of the platelet-derived and monocyte-derived growth factors that induce migration of smooth muscle cells from the media into the intima, where they replicate, synthesize connective tissue and proteoglycans and form a fibrous plaque. Other cells (e.g., macrophages, endothelial cells, arterial smooth muscle cells) also produce growth factors that can contribute to smooth muscle hyperplasia and extracellular matrix production.

Atherosclerotic plaque generally grow slowly and over time may produce a severe stenosis (a narrowing of the diameter of the artery) or may progress to total arterial occlusion. With time, the plaque becomes calcified. Some plaques are stable, but others, especially those rich in lipids and inflammatory cells (e.g., macrophages) and covered by a thin fibrous cap, may undergo spontaneous fissure or rupture, exposing the plaque contents to flowing blood. These plaques are deemed to be unstable or vulnerable and are more closely associated to the onset of an acute ischemic event. The ruptured plaque stimulates thrombosis; the thrombi may embolize, rapidly occlude the lumen to precipitate a heart attack or an acute ischemic syndrome, or gradually become incorporated into the plaque, contributing to its stepwise growth.

Atherosclerosis is characteristically silent until critical stenosis, thrombosis, aneurysm, or embolus supervenes. Initially, symptoms and signs reflect an inability of blood flow to the affected tissue to increase with demand (e.g., angina or exertion, intermittent claudication). Symptoms and signs commonly develop gradually as the atheroma slowly encroaches on the vessel lumen. However, when a major artery is acutely occluded, the results can be serious, such as, for example, infarction of heart muscle as described above.

Traditional therapy for prevention or inhibition of cardiovascular and cerebrovascular complications of atherosclerosis are reversing, to the extent possible, the risk factors associated with atherosclerosis such as cigarette smoking, obesity, abnormal serum levels (LDL cholesterol levels), hypertension, diabetes mellitus, hyperhomocysteinemia and possibly *C. pneumoniae*, infection. Hence treatment to date, is generally directed to the complications of atherosclerosis including angina pectoris, myocardial infarction, arrhythmias, heart failure, kidney failure, ischemic stroke, and peripheral arterial occlusion.

Further, vascular intervention, including angioplasty, stenting, atherectomy and grafting is often complicated by endothelial and smooth muscle cell proliferation resulting in restenosis or re-clogging of the artery. This may be due to endothelial cell injury caused by the treatment itself. Treatment of restenosis often involve a second angioplasty or bypass surgery. The drawbacks of such treatment are obvious including the risk of repeat restenosis.

For example, angioplasty involves insertion of a balloon-tipped catheter into an artery at the site of a partially obstructive atherosclerotic lesion. Inflation of the balloon is intended to rupture the intima and media and dilate the obstruction. About 20 to 30% of obstructions reocclude in just a few days or weeks. Eltchaninoff et al., *Balloon Angioplasty For In-Stent Restenosis*, 1998, *J. Am Coll. Cardiol.*, 32(4): 980-984. Use of stents reduces the reocclusion rate, however a significant percentage continue to result in restenosis. The rate of stenosis after angioplasty is dependent upon a number of factors including the length of the plaque. Stenosis rates vary from 10% to 35% depending the risk factors present. Further, repeat angiography one year later reveals an apparently normal lumen in only about 30% of vessels undergoing the procedure.

In terms of the biological mechanism and characteristics leading to restenosis, accumulation of extracellular matrix containing collagen and proteoglycans in association with smooth muscle cells characterizes both the atheroma and the arterial hyperplastic lesion that lead to restenosis after balloon injury or clinical angioplasty. Some of the delay in luminal narrowing with respect to smooth muscle cell proliferation may result from the continuing elaboration of matrix materials by neointimal smooth muscle cells. Various mediators may alter matrix synthesis by smooth muscle cells in vivo. A "cascade mechanism" has been proposed for restenosis. In this model, an injurious stimulus induces expression of growth-stimulatory cytokines such as interleukin 1 and tumor necrosis factor. Libby et al., *Cascade Model of Restenosis* 1992, Circulation 86(6): III-47-III52.

More specifically, the acute local thrombosis, blood coagulation and/or mechanical injury appear to activate cyto gene expression by macrophages and/or smooth muscle cells within the plaque. This acute cytokine expression evokes secondary, self-sustaining and continuing autocrine and paracrine growth factor and cytokine expression by lesional cells including leukocytes. For example, both vascular endothelial and smooth muscle cells can express genes encoding both isoforms of the multipotent cytokine IL-1. Smooth muscle cells can also express the gene encoding TNF-α. Activated endothelial cells and smooth muscle cells both elaborate the B and T cell activator IL-6. IL-6 accounts for almost 4% of the newly synthesized proteins secreted by smooth muscle cells stimulated by IL-1. Human vascular wall cells also produce the monocyte chemoattractant and activator monocyte chemoattractant protein-1 (MCP-1)/JE (also known as macrophage chemoattractant and activating factor) and the monocyte differentiation and activating factor M-CSF (a macrophage colony stimulating factor).

Various therapies have been attempted to treat or prevent restenosis. For example, it has been reported that, since oxidizing metabolites may induce chain reactions that may lead to restenosis, multivitamins having antioxidant properties (30,000 IU of beta carotene, 500 mg of vitamin C and 700 IU of vitamin E) and/or probucol (500 mg) were studied. They were administered twice daily for four weeks prior and six months after angioplasty, Tardif et al., *N. Engl. J. Med.*: 337(6): 365-72 (1997). The antioxidant vitamins alone had no effect. Probucol did reduce the rate of restenosis after angioplasty by almost 50%. However, probucol has removed from the U.S. market for reducing HDL cholesterol levels, and causing heart rhythm disturbances which might lead to dangerous arrhythmias.

Intracoronary irradiation during angioplasty and stent implantation to reduce the instances of restenosis have likewise been studied. Limitations include, for example, handling stents filled with radioactive liquid (Re 188-radioactive rhenium). Further, studies show that this strategy may need to be tailored to stent design for proper distribution for the absorption and scattering of beta emitters. Amols et al., (1998) Circulation, 98:2024-2029.

Clearly, there remains a great need for therapies directed to the prevention and treatment of atherosclerosis, restenosis and related disorders.

3. SUMMARY OF THE INVENTION

The present invention includes methods and compositions for the treatment or prevention of atherosclerosis, including diseases of the cardiovascular and renal systems, and in particular, the treatment or prevention of restenosis after vascular intervention such as angioplasty. One embodiment of the present invention includes the administration of compounds including thalidomide, its analogs, its hydrolysis products, its metabolites, its derivatives or precursors of thalidomide to treat or prevent atherosclerosis or the causes thereof, including stenosis. Compounds used in the invention typically exhibit TNF-α inhibitory activity. Administration as used in the invention includes oral, ophthalmic, (including intravitreal or intracameral), topical, mucosal (including buccal, rectal, vaginal, nasal and sublingual), transdermal or parenteral (including subcutaneous, intramuscular, intravenous, bolus injection, intradermal, intratracheal, and epidural) administration.

In another embodiment, the present invention relates to a prosthetic device suitable for use or implantation into a subject, preferably a human. The device is coated with a composition containing the compounds of the invention. The device is preferably a stent. The formulated materials used in accordance with the present invention comprise thalidomide, its analogs and other TNF-α inhibitors. These compositions are biocompatible.

Finally, the invention includes the combined use of a prophylatic or therapeutic administration of a compound of the invention in conjunction with the use of a stent coated with a compound of the invention during surgery or implantation.

4. DETAILED DESCRIPTION OF THE INVENTION

The present invention includes methods and compositions for the treatment or prevention of atherosclerosis, including diseases of the cardiovascular and renal systems, and in particular, the treatment or prevention of restenosis after vascular intervention such as angioplasty. One embodiment of the present invention includes the administration of thalidomide or analogs, hydrolysis products, metabolites and precursors of thalidomide.

In 1953, N-phthaloyl-α-aminoglutarimide, commonly known as thalidomide, was discovered. Thalidomide was thought to be free from the dangerous side effects associated with barbiturates and was marketed in the late 1950's as a sedative. The notoriety of thalidomide is based upon its significant teratogenic effects discovered upon its administration to pregnant woman for morning sickness outside the United States (thalidomide was not approved in the United States due to possible peripheral neuropathic side effects not associated with its teratogenic effects). In spite of thalidomide's tragic start as a therapeutic, thalidomide has been extensively studied and found to posses a number of therapeutic properties.

Thalidomide's anti-inflammatory effects were first noted as early as 1965. Skeskin *J. Clin. Pharmacol. Ther.* 6:303 (1965). More specifically, thalidomide was found to be extremely effective for the treatment of erythema nodosum leprosum (ENL), an acute inflammatory manifestation of lepromatous leprosy. More recently, thalidomide was found to exert immunomodulatory and anti-inflammatory effects in a variety of disease states, including graft-versus-host disease following bone marrow transplantation, rheumatoid arthritis, inflammatory bowel disease (IBD), cachexia in AIDS, and opportunic infections in AIDS. In studies to define the physiological targets of thalidomide, the drug was found to have a wide variety of biological activities exclusive of its sedative effect including neurotoxicity, teratogenicity, suppression of TNF-α production by monocytes/macrophages and the accompanying inflammatory toxicities associated with high levels of TNF-α, and inhibition of angiogenesis and neovascularization.

Additionally, beneficial effects have been observed in a variety of dermatological conditions, ulcerative colitis, Crohn's disease, Behçets's syndrome, systemic lupus erythematosis, rheumatoid arthritis, aphthous ulcers, and lupus. Recently published results demonstrated the anti-angiogenic properties of thalidomide in in vivo models. D'Amato et al., *Thalidomide Is An Inhibitor Of Angiogenesis*, 1994, PNAS, USA 91:4082-4085. Further preclinical and clinical trials in treatment of cancer and in AIDS related conditions are ongoing.

The present invention adds to the field of uses for thalidomide and its derivatives for therapies directed to atherosclerosis, restenosis and related disorders.

4.1 The Compounds of the Invention

The preferred compounds of the invention are thalidomide, as well as analogs, hydrolysis products, metabolites, derivatives and precursors of thalidomide. Some of these compounds may be teratogenic (and thus must be used with the proper safeguards). However, it is to be understood that it is not necessary for a compound to have teratogenic activity to be considered part of the present invention.

Compounds useful in the present invention may also typically exhibit TNF-α inhibitory activity. The compounds of the invention include cyano and carboxy derivatives of substituted styrenes including those found in U.S. Pat. No. 5,929,117; the cyclic imides (particularly those described in Muller, *Thalidomide: From tragedy to new drug discovery*, Chemtech 27(1):21-25(1997) which is incorporated by reference in its entirety) found in U.S. Pat. No. 5,605,914; the cycloalkyl amides and cycloalkyl nitrites of U.S. Pat. Nos. 5,728,844 and 5,728,845, respectively; the aryl amides (for example, an embodiment being N-benzoyl-3-amino-3-(3',4'-dimethoxyphenyl)propanamide) of U.S. Pat. Nos. 5,801,195 and 5,736,570; the 1-oxo-2-(2,6-dioxo-3-fluoropiperidin-3yl) isoindolines and 1,3-dioxo-2-(2,6-dioxo-3-fluoropiperidine-3-yl) isoindolines of U.S. Pat. No. 5,874,448; the tetra substituted 2-(2,6-dioxopiperdin-3-yl)-1-oxoisoindolines of U.S. Pat. No. 5,798,368; the imide/amide ethers and alcohols (for example 3-phthalimido-3-(3',4'-dimethoxypheryl)propan-1-ol) of U.S. Pat. No. 5,703,098 and the succinimides and maleimides (for example methyl 3-(3',4',5'6'-petrahydrophthalimdo)-3-(3",4"-dimethoxyphenyl) propionate) as found in U.S. Pat. No. 5,658,940; 1-Oxo and 1,3 dioxo-2-(2,6-dioxopiperidin-3 yl) isoindolines as described in Reexamined U.S. Pat. No. B 5,635,517 Certificate issued Jun. 29, 1999; a class of non-polypeptide cyclic amides disclosed in U.S. Pat. Nos. 5,698,579 and 5,877,200; imido and amido substituted alkanohydroxamic acids found in WO 99/06041 and substituted phenethylsulfones disclosed in pending U.S. application Ser. No. 09/183, 049; thalidomide, as well as its analogs, its hydrolysis products, its metabolites and its precursors of thalidomide such as those described in D'Amato, U.S. Pat. Nos. 5,593, 990, 5,629,327, and 5,874,448. Each of the above described United States patents and applications are incorporated by reference in their entireties.

In one embodiment, the preferred compounds are thalidomide, as well as its analogs, its hydrolysis products, its metabolites and its precursors of thalidomide such as those described in D'Amato, U.S. Pat. Nos. 5,593,990, 5,629,327, and 5,874,448 each of which is incorporated by reference in their entirety, including but not limited to compounds having the following structures:

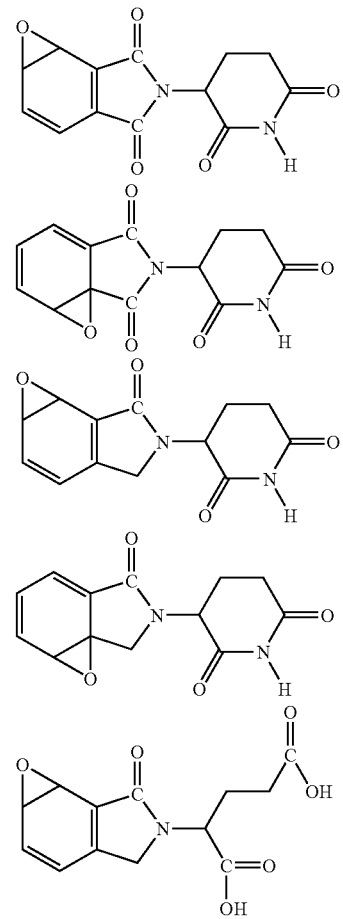

-continued

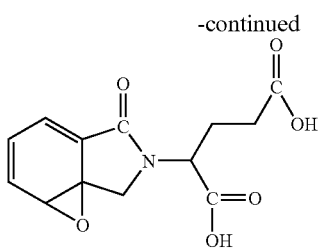

It should be understood that the epoxide can be attached at the 6,1 site on the benzene ring, the 1,2 site, the 2,3 site 3,4 or the 4,5 site.

The above epoxides can be hydrolized to the following compounds which are also useful in the present invention:

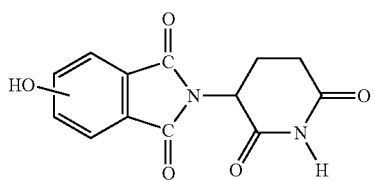

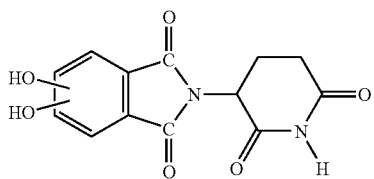

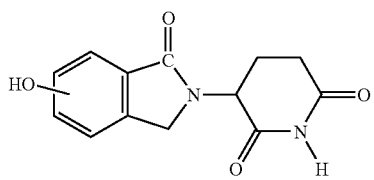

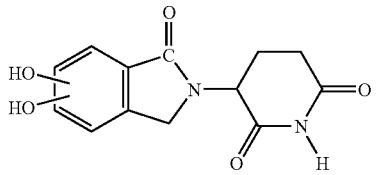

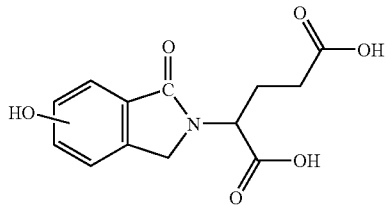

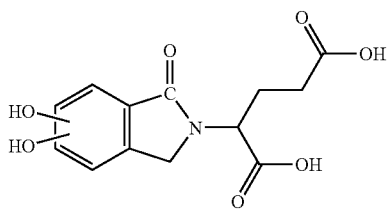

All of these compounds are contemplated as part of the present invention. Other preferred embodiments include 1-Oxo-and 1,3 dioxo-2-(2,6-dioxopiperidin-3-yl) isoindolines substituted with amino in the benzo ring as described in Reexamined U.S. Pat. No. B 5,635,517 Certificate issued Jun. 29, 1999 for U.S. Pat. No. 5,635,517 originally issued Jun. 3, 1997, which are incorporated in their entireties. These compounds have the structure:

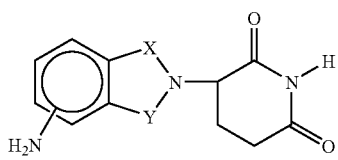

in which one of X and Y is C=O and the other of X and Y is C=O or $CH_2$

Particularly preferred compounds include:
1-oxo-2-(2,6-dioxopiperidin-3-yl)-5-aminoisoindoline
1-oxo-2-(2,6-dioxopiperidin-3-yl)-4-aminoisoindoline
1-oxo-2-(2,6-dioxopiperidin-3-yl)-6-aminoisoindoline
1-oxo-2-(2,6-dioxopiperidin-3-yl)-5-aminoisoindoline
1,3dioxo-2-(2,6-dioxopiperidin-3-yl)-4-aminoisoindoline
1,3dioxo-2-(2,6-dioxopiperidin-3-yl)-5-aminoisoindoline Other preferred compounds include a class of non-polypeptide cyclic amides disclosed in U.S. Pat. Nos. 5,698,579 and 5,877,200 which are incorporated herein in their entirety. Representative cyclic amides include compounds of the formula:

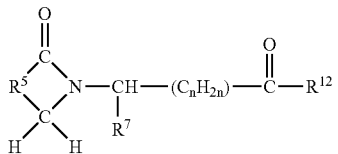

in which:

n has a value of 1, 2, or 3;

$R^5$ is o-phenylene, unsubstituted or substituted with 1 to 4 substituents each selected independently from the group consisting of nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkyl of 1 to 10 carbon atoms, and halo;

$R^7$ is (i) phenyl or phenyl substituted with one or more substituents each selected independently of the other from the group consisting of nitro, cyano, trifluoromethyl, carbethoxy, carbomethoxy, carbopropoxy, acetyl, carbamoyl acetoxy, carboxy, hydroxy, amino, alkyl of 1 to 10 carbon atoms, aloxy of 1 to 10 carbon atoms, and halo, (ii) benzyl unsubstituted or substituted with 1 to 3 substituents selected from the group consisting of nitro, cyano, trifluoromethyl, carbothoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, (iii) naphthyl, and (iv) benzyloxy;

$R^{12}$ is —OH, alkoxy of 1 to 12 carbon atoms, or

$R^8$ is hydrogen or alkyl of 1 to 10 carbon atoms; and
$R^9$ is hydrogen, alkyl of 1 to 10 carbon atoms, —$COR^{10}$, or —$SO_2R^{10}$ in which
$R^{10}$ is hydrogen, alkyl of 1 to 10 carbon atoms, or phenyl.
Specific preferred compounds of this class include but are not limited to:
3-phenyl-2-(1-oxoisoindolin-2-yl)propionic acid;
3-phenyl-2-(1-oxoisoindolin-2-yl)propionamide;
3-phenyl-3-(1-oxoisoindolin-2-yl)propionic acid;
3-phenyl-3-(1-oxoisoindolin-2-yl)propionamide;
3-(4-methoxyphenyl)-3-(1-oxisoindolin-yl)propionic acid;
3-(4-methoxyphenyl)-3-(1-oxisoindolin-yl)propionamide;
3-(3,4dimethoxyphenyl)-3-(1-oxisoindolin-2-yl)propionic acid;
3-(3,4-dimethoxyphenyl)-3-(1-oxisoindolin-2-yl)propionamide;
3-(3,4-diethoxyphenyl)-3-(1-oxoisoindolin-yl)propionic acid;
methyl 3-(1-oxoisoindolin-2-yl)-3-(3-ethoxy-4-methoxyphenyl)propionate;
3-(1-oxoisoindolin-2-yl)-3-(3-ethoxy-4-methoxyphenyl) propionic acid;
3-(1-oxoisoindolin-2-yl)-3-(3-propoxy-4-methoxyphenyl)propionic acid;
3-(1-oxoisoindolin-2-yl)-3-(3-butoxy-4-methoxyphenyl) propionic acid;
3-(1-oxoisoindolin-2-yl)-3-(3-propoxy-4-methoxyphenyl)propionamide;
3-(1-oxoisoindolin-2-yl)-3-(3-butoxy-4-methoxyphenyl) propionamide;
methyl 3-(1-oxoisoindolin-2-yl)-3-(3-butoxy-4-methoxyphenyl)propionate; and
methyl 3-(1-oxoisoindolin-2-yl)-3-(3-propoxy-4-methoxyphenyl)propionate.

Other preferred compounds for use in the invention include the imido and amido substituted alkanohydroxamic acids found in WO 99/06041, which is also incorporated by reference in its entirety, including:

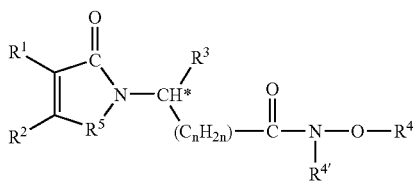

wherein:
each of $R^1$ and $R^2$, when taken independently of each other, is hydrogen, lower alkyl, or $R^1$ and $R^2$, when taken together, together with the depicted carbon atoms to which each is bound, is o-phenylene, o-naphthylene, or cyclohexene-1,2-diyl, unsubstituted or substituted with 1 to 4 substituents each selected independently from the group consisting of nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, and halo;
$R^3$ is phenyl substituted with from one to four substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, alkylthio of 1 to 10 carbon atoms, benzyloxy, cycloalkoxy of 3 to 6 carbon atoms, $C_4$-$C_6$-cycloalkylidenemethyl, $C_3$-$C_{10}$-alkylidenemethyl, indanyloxy, and halo;
$R^4$ is hydrogen, alkyl of 1 to 6 carbon atoms, phenyl, or benzyl;
$R^{4'}$ is hydrogen or alkyl of 1 to 6 carbon atoms;
$R^5$ is —$CH_2$—, —$CH_2$—CO—, —$SO_2$—, —S—, or —NHCO—; and
n has a value of 0, 1, or 2; and
(b) the acid addition salts of said compounds which contain a nitrogen atom capable of being protonated.

Particularly preferred compounds include but are not limited to:
3-(3-ethoxy-4-methoxyphenyl)-N-hydroxy-3-(1-oxoisoindolinyl)propionamide;
3-(3-ethoxy-4-methoxyphenyl)-N-methoxy-3-(1-oxoisoindolinyl)propionamide;
N-benzyloxy-3-(3-ethoxy-4-methoxyphenyl)-3-phthalimidopropionamide;
N-benzyloxy-3-(3-ethoxy-4-methoxyphenyl)-3-(3-nitrophthalimido)propionamide;
N-benzyloxy-3-(3-ethoxy-4-methoxyphenyl)-3-(1-oxoisoindolinyl)propionamide;
3-(3-ethoxy-4-methoxyphenyl)-N-hydroxy-3-phthalimidopropionamide;
N-hydroxy-3-(3,4-dimethoxyphenyl)-3-phthalimidopropionamide;
3-(3-ethoxy-4-methoxyphenyl)-N-hydroxy-3-(3-nitrophthalimido)propionamide;
N-hydroxy-3-(3,4-dimethoxyphenyl)-3-(1-oxoisoindolinyl)propionamide;
3-(3-ethoxy-4-methoxyphenyl)-N-hydroxy-3-(4-methylphthalimido)propionamide;
3-(3-cyclopentyloxy-4-methoxyphenyl)-N-hydroxy-3-phthalimidopropionamide;
3-(3-ethoxy-4-methoxyphenyl)-N-hydroxy-3-(1,3-dioxo-2,3-dihydro-1H-benzo[f]isoindol-2-yl)propionamide;
N-hydroxy-3-{3-9(2-propoxy)-4-methoxyphenyl}-3-phthalimidopropionamide;
3-(3-ethoxy-4-methoxyphenyl)-3-(3,6-difluorophthalimido)-N-hydroxypropionamide;
3-(4-aminophthalimido)-3-(3-ethoxy-4-methoxyphenyl)-N-hydroxypropionamide;
3-(3-aminophthalimido)-3-(3-ethoxy-4-methoxyphenyl)-N-hydroxypropionamide;
N-hydroxy-3-(3,4-dimethoxyphenyl)-3-(1-oxoisoindolinyl)propionamide;
3-(3-cyclopentyloxy-4-methoxyphenyl)-N-hydroxy-3-(1-oxoisoindolinyl)propionamide; and
N-benzyloxy-3-3-ethoxy-4-methoxyphenyl)-3-(3-nitrophthalimido)propionamide.

Additional preferred compounds are inhibitors of nuclear factor κB (NFκB). NFκB has been implicated as a transcriptional activator in a variety of disease and inflammatory states and is thought to regulate cytokine levels including but not limited to TNF-α and also to be an activator of HIV transcription (Dbaibo, et al., *J Biol. Chem.* 1993, 17762-66;

Duh et al., *Proc. Natl. Acad. Sci.* 1989, 86, 5974-78; Bachelerie et al., *Nature* 1991, 350, 709-12; Suzuki et al., *Biochem And Biophys. Res. Comm.* 1993, 193, 277-83). Such preferred compounds include the substituted phenethylsulfones substituted to the phenyl group with a oxoisoindine group such as those found in pending U.S. patent application Ser. No. 09/183,049 and are as follows:

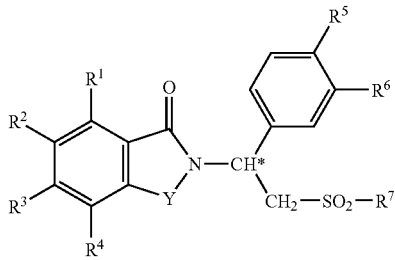

in which
  the carbon atom designated * constitutes a center of chirality;
  Y is C=O, CH2, $SO_2$, or $CH_2C=O$;
  each of $R^1$, $R^2$, $R^3$, and $R^4$, independently of the others, is hydrogen, halo, alkyl of 1 to 4 carbon atoms, alkoxy of 1 to 4 carbon atoms, nitro, cyano, hydroxy, or —$NR^8R^9$; or any two of $R^1$, $R^2$, $R^3$, and $R^4$ on adjacent carbon atoms, together with the depicted phenylene ring are naphthylidene;
  each of $R^5$ and $R^6$, independently of the other, is hydrogen, alkyl of 1 to 4 carbon atoms, alkoxy of 1 to 4 carbon atoms, cyano, or cycloalkoxy of up to 18 carbon atoms;
  $R^7$ is hydroxy, alkyl of 1 to 8 carbon atoms, phenyl, benzyl, or $NR^8R^9$;
  each of $R^8$ and $R^9$ taken independently of the other is hydrogen, alkyl of 1 to 8 carbon atoms, phenyl, or benzyl, or one of $R^8$ and $R^9$ is hydrogen and the other is —$COR^{10}$ or —$SO_2R^{10}$, or $R^8$ and $R^9$ taken together are tetramethylene, pentamethylene, hexamethylene, or —$CH_2CH_2X^1CH_2CH_2$— in which $X^1$ is —O—, —S— or —NH—; and
  each of $R^{8'}$ and $R^{9'}$ taken independently of the other is hydrogen, alkyl of 1 to 8 carbon atoms, phenyl, or benzyl, or one of $R^{8'}$ and $R^{9'}$ is hydrogen and the other is —$COR^{10'}$ or —$SO_2R^{10'}$, or $R^{8'}$ and $R^{9'}$ taken together are tetramethylene, pentamethylene, hexamethylene, or —$CH_2CH_2X^2CH_2CH_2$— in which $X^2$ is —O—, —S—, or —NH—.

It will be appreciated that while for convenience the above compounds are identified as phenethylsulfones, they include sulfonamides when $R^7$ is $NR^8R^9$.

Preferred groups of such compounds are those in which Y is C=O; and
  Y is $CH_2$.

A further preferred group of such compounds are those in which each of $R^1$, $R^2$, $R^3$, and $R^4$ independently of the others, is hydrogen, halo, methyl, ethyl, methoxy, ethoxy, nitro, cyano, hydroxy, or —$NR^8R^9$ in which each of $R^8$ and $R^9$ taken independently of the other is hydrogen or methyl or one of $R^8$ and $R^9$ is hydrogen and the other is —$COCH_3$.

A further preferred group of such compounds are those in which one of $R^1$, $R^2$, $R^3$, and $R^4$ is —$NH_2$ and the remaining of $R^1$, $R^2$, $R^3$, and $R^4$ are hydrogen.

A further preferred group of such compounds are those in which one of $R^1$, $R^2$, $R^3$, and $R^4$ is —$NHCOCH_3$ and the remaining of $R^1$, $R^2$, $R^3$, and $R^4$ are hydrogen.

A further preferred group of such compounds are those in which one of $R^1$, $R^2$, $R^3$, and $R^4$ is —$N(CH_3)_2$ and the remaining of $R^1$, $R^2$, $R^3$, and $R^4$ are hydrogen A further preferred group of such compounds are those in which one of $R^1$, $R^2$, $R^3$, and $R^4$ is methyl and the remaining of $R^1$, $R^2$, $R^3$, and $R^4$ are hydrogen.

A further preferred group of such compounds are those in which one of $R^1$, $R^2$, $R^3$, and $R^4$ is fluoro and the remaining of $R^1$, $R^2$, $R^3$, and $R^4$ are hydrogen.

A further preferred group of such compounds are those in which each of $R^5$ and $R^6$, independently of the other, is hydrogen, methyl, ethyl, propyl, methoxy, ethoxy, propoxy, cyclopentoxy, or cyclohexoxy.

A further preferred group of such compounds are those in which $R^5$ is methoxy and $R^6$ is monocycloalkoxy, polycycloalkoxy, and benzocycloalkoxy.

A further preferred group of such compounds are those in which $R^5$ is methoxy and $R^6$ is ethoxy.

A further preferred group of such compounds are those in which $R^7$ is hydroxy, methyl, ethyl, phenyl, benzyl, or $NR^{8'}R^{9'}$ in which each of $R^{8'}$ and $R^{9'}$ taken independently of the other is hydrogen or methyl.

A further preferred group of such compounds are those in which $R^7$ is methyl, ethyl, phenyl, benzyl or $NR^{8'}R^{9'}$ in which each of $R^{8'}$ and $R^{9'}$ taken independently of the other is hydrogen or methyl.

A further preferred group of such compounds are those in which $R^7$ is methyl.

A further preferred group of such compounds are those in which $R^7$ is $NR^{8'}R^{9'}$ in which each of $R^{8'}$ and $R^{9'}$ taken independently of the other is hydrogen or methyl. Specific preferred compounds of this class include but are not limited to:

2-[1(-3-ethoxy-4-methoxyphenyl)-2-methyl-sulfonylethyl]isoindolin-1-one,

2-[1-(3-ethoxy-4-methoxyphenyl)-2-(N,N-dimethyl-aminosulfonyl)ethyl]isoindolin-1-one, 2-[1-(3-ethoxy-4-methoxyphenyl)-2-methyl-sulfonylethyl]isoindoline-1,3-dione, 2-[1-(3-ethoxy-4-methoxyphenyl)-2-methyl-sulfonylethyl]-5-nitro-isoindoline-1,3-dione, 2-[1-(3-ethoxy-4-methoxyphenyl)-2-methyl-sulfonylethyl]-4-nitroisoindoline-1,3-dione, 2-[1-(3-ethoxy-4-methoxyphenyl)-2-methylsulfonylethyl]-4-aminoisoindoline-1,3-dione, 2-[1-(3-ethoxy-4-methoxyphenyl)-2-methylsulfonylethyl]-5-methylisoindoline-1,3-dione, 2-[1-(3-ethoxy-4-methoxyphenyl)-2-methylsulfonylethyl]-5-acetamidoisoindoline-1,3-dione, 2-[1-(3-ethoxy-4-methoxyphenyl)-2-methylsulfonylethyl]-4-dimethylaminoisondoline-1,3-dione, 2-[1-(3-ethoxy-4-methoxyphenyl)-2-methylsulfonylethyl]-5-dimethylaminoisoindoline-1,3-dione, 2-[1-(3-ethoxy-4-methoxyphenyl)-2-methylsulfonylethyl]benzo[e]isoindoline-1,3-dione, 2-[1-(3-ethoxy-4-methoxyphenyl)-2-methylsulfonylethyl]-4-methoxyisoindoline-1,3-dione, 1-(3-cyclopentyloxy-4-methoxyphenyl)-2-methylsulfonyl-ethyl-amine, 2-[1-(3-cyclopentyloxy-4-methoxyphenyl)-2-methylsulfonylethyl]isoindoline-1,3-dione, and 2-[1-(3-cyclopentyloxy-4-methoxyphenyl)-2-methylsulfonylethyl]-4-dimethylaminoisoindoline-1,3-dione.

Many of the compounds that are contemplated as part of the present invention can be enriched in optically active enantiomers of the compounds specified above using standard resolution or asymetric synthesis known in the art. Blaschke, for example, has reported that the S enantiomers may be disproportionately responsible for the dismelia-producing effect of thalidomide and its analogs. See, generally Blaschke, *Arzneimittelforschung* 29:1640-1642 (1979). Procedures to obtain optically active preparations of the compounds of interest can be found in the literature. See, e.g., Shealy et al., *Chem. Indus.* 1030 (1965); and Casini et al., *Farmaco Ed. Sci.* 19:563 (1964).

Compounds of the invention can either be commercially purchased or prepared according to the methods described in the patents or patent publications disclosed herein. For example, U.S. Pat. No. 5,635,517 describes the methods of preparing optical isomers of 1,3-dioxo-2-(2,6-dioxopiperidin-3-yl) isoindoline substituted with amino in the benzo ring. 1,3-Dioxo-2-(2,6-dioxopiperidin-3-yl) isoindoline substituted with amino in the benzo ring possess a center of chirality and can exist as optical isomers. Both the racemates of these isomers and the individual isomers themselves are within the scope of the present invention. The racemates can be used as such or can be separated into their individual isomers mechanically as by chromatography using a chiral absorbant. Alternatively, the individual isomers can be prepared in chiral form or separated chemically from a mixture by forming salts with a chiral acid, such as the individual enantiomers of 10-camphorsulfonic acid, camphoric acid, α-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as to obtain either or both substantially free of the other; i.e., in a form having an optical purity of >95%.

Alternatively, 1,3-dioxo-2-(2,6-dioxopiperidin-3-yl) isoindoline substituted with amino in the benzo ring can be stereopreferentially synthesized by allowing the lower alkyl 2-(bromomethyl)nitrobenzoate intermediate to react with either (R)-1-benzyloxy-2,6-dioxo-3-tert.-butoxycarbonylaminopiperidine or (S)-1-benzyloxy-2,6-dioxo-3-tert.-butoxycarbonylaminopiperidine analogous to the method described by Robin et al., Tetrahedron Asymmetry, 6, 1249 (1995). Hydrogenation in this case not only reduces the nitro group to an amino group but also converts the N-benzyloxy group to an N-hydroxy group which can be removed with bromoacetophenone triethylamine and dimethylaminopyridine to yield the corresponding (R) or (S) enantiomer.

The present invention also pertains to the physiologically acceptable non-toxic acid addition salts of the compounds thereof Such salts include those derived from organic and inorganic acids or bases know in the art: such acids include for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds of the invention that are acidic in nature are capable of forming salts with various pharmaceutically acceptable bases. The bases that can be used to prepare pharmaceutically acceptable base addition salts of such acidic compounds of the invention are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

Certain of these compounds, such as thalidomide are commercially available (Thalomid™, Celgene, Inc., Warren, N.J.). Other above compounds can be made by methods known in the art, including those disclosed in the patents cited above which are incorporated by reference in their entries.

Clearly, the most preferred compound of the invention is thalidomide.

4.2 Compositions, Formulations, and Routes of Administration

The compounds described above can be provided as pharmaceutically acceptable formulations using formulation methods known to those of ordinary skill in the art. Administration as used in the invention includes those suitable for oral, ophthalmic, (including intravitreal or intracameral), topical, mucosal (including buccal, rectal, vaginal, nasal and sublingual), transdermal or parenteral (including subcutaneous, intramuscular, intravenous, bolus injection, intradermal, intratracheal, and epidural) administration. In addition, the combinations may be incorporated into biodegradable polymers allowing for sustained release of the compound, the polymers being implanted in the vicinity of where drug delivery is desired. Biodegradable polymers and their use are described, for example, in detail in Brem et al., *J. Neurosurg.* 74:441-446 (1991).

The formulations include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a flee-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

Oral dosage forms include tablets, capsules, dragees, and similar shaped, compressed pharmaceutical forms containing from about 1 ng to 300 mg of drug per unit dosage. Isotonic saline solutions can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds described above and are associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients, include but are not limited to lactose, dextrose, sucrose, sorbitol, mannitol, starch, gum acacia, calcium silicate, microcrystalline cellulose, polyvinlypyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

In additional to the common dosage forms set out above, the compounds can also be administered by controlled release means or delivery devices that are well known to those or ordinary skill in the art, such as those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, the disclosures of which are incorporated herein by reference. These dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected fro use with the pharmaceutical compositions of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug. In addition, controlled-release formulations can be used to affect the time of onset of action or other characteristics, such as blood levels of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body. Controlled-release of an active ingredient can be stimulated by various inducers, including, but not limited to, pH, temperature, enzymes, water, or other physiological conditions or compounds.

4.3 Therapies for Atherosclerosis and Related Conditions

4.3.1 Treatment for the Prevention or Reduction of Atherosclerosis

Those at high risk, having for example, a number of the risk factors described above in the background section, may be appropriate candidates for the therapies of the invention.

The compounds may be used to inhibit or treat all forms of conditions involving atherosclerosis. In a preferred embodiment the invention includes a therapy to reduce or prevent the degree of restenosis after vascular intervention such as angioplasty, stenting, atherectomy and grafting. All forms of vascular intervention are contemplated by the invention including diseases of the cardiovascular and renal system. The following chart provides a listing of the major systemic arteries that may be in need of treatment, all of which are contemplated by the invention:

TABLE I

| Major Systemic Arteries | |
|---|---|
| Artery | Body Areas Supplied |
| Axillary | Shoulder and axilla |
| Brachial | Upper arm |
| Brachiocephalic | Head, neck, and arm |
| Celiac | Divides into left gastric, splenic, and hepatic arteries |
| Common carotid | Neck |
| Common iliac | Divides into external and internal iliac arteries |
| Coronary | Heart |
| Deep femoral | Thigh |
| Digital | Fingers |
| Dorsalis pedis | Foot |
| External carotid | Neck and external head regions |
| External iliac | Femoral artery |
| Femoral | Thigh |
| Gastric | Stomach |
| Hepatic | Liver, gallbladder, pancreas, and duodenum |
| Inferior mesenteric | Descending colon, rectum, and pelvic wall |
| Internal carotid | Neck and internal head regions |
| Internal iliac | Rectum, urinary bladder, external genitalia, buttocks muscles, uterus and vagina |
| Left gastric | Esophagus and stomach |
| Middle sacral | Sacrum |
| Ovarian | Ovaries |
| Palmar arch | Hand |
| Peroneal | Calf |
| Popliteal | Knee |
| Posterior tibial | Calf |
| Pulmonary | Lungs |
| Radial | Forearm |
| Renal | Kidney |
| Splenic | Stomach, pancreas, and spleen |
| Subclavian | Shoulder |
| Superior mesenteric | Pancreas, small intestine, ascending and transverse colon |

TABLE I-continued

| Major Systemic Arteries | |
|---|---|
| Artery | Body Areas Supplied |
| Testicular | Testes |
| Ulnar | Forearm |

The optimal dosage to be administered will be readily determined by those skilled in the art and will vary on the condition being treated, the particular TNF-α inhibitor and mode of administration. Other factors include the weight and condition of the human or animal. It is to be understood that the present invention has application for both human and veterinary use. For oral administration to humans, a dosage of between approximately 0.01 to 300 mg/kg/day.

In this embodiment, the compound or composition such as a thalidomide composition is administered orally to a patient at risk for complications caused by atherosclerosis. Typically, those at risk include those having one or more of the following conditions: abnormal serum lipid levels, hypertension, cigarette smoking, diabetes mellitus, obesity, physical inactivity, hyperhomocysteinemia and chlamydia pneumoniae infection. The compound is thus administered prophylactically to prevent serious complications or to avoid the need for surgical intervention.

4.3.2 Treatment for the Prevention or Reduction of Restenosis

Macrophage appear to infiltrate restenotic lesions of coronary arteries. For example, in one study macrophage areas, but neither smooth muscle cell nor tissue factor areas, were significantly larger in primary lesions that develop restenosis when compared to primary lesions that did not develop into restenosis after coronary atherectomy. Moreno et al., *Macrophage Infiltration Predicts Restenosis After Coronary Intervention in Patients with Unstable Angina*, 1996, Circulation 94(12):3098-3102.

Further, it has been suggested the level of macrophage colony stimulating factor (M-CSF) in the atherectomy tissue can indicate, or predict the likelihood or degree of restenosis in post vascular intervention tissue. Takano et al., *High levels of circulating Macrophage Colony Stimulating Factor (M-CSF) Predict Restenosis After Primary Angioplasty in Patients With Acute Myocardial Infraction*, 1998 Circulation, 98 (17, Supp): 4437.

Thus, the invention encompasses the use of the compounds of the invention in patients having abnormally high levels of circulating macrophage colony stimulating factor (M-CSF) prior to vascular intervention. This treatment may avoid the need for or facilitate vascular intervention.

All forms of vascular intervention are contemplated by the invention, including for example, renal angioplasty, percutaneous coronary intervention (PCI), percutaneous transluminal coronary angioplasty (PTCA); carotid percutaneous transluminal angioplasty (PTA); coronary by-pass grafting, angioplasty with stent implantation, peripheral percutaneous transluminal intervention of the iliac, femoral or popliteal arteries, surgical intervention using impregnated artificial grafts and the like.

The magnitude of a therapeutic dose of the compound will vary with the severity of the condition being treated, the route of administration and the particular compound being administered. Additionally, the dose, and dose frequency will also vary according to the age, body weight and general condition of the individual patient. In general, the administration will begin just prior to (~12 hours) or during the angioplasty and will typically continue for 4 to 12 weeks. The daily dose range of the compound administered orally is between 0.01 to 300 mg/kg/day.

A dosage regime following angioplasty may be desired and may be necessary in the case of emergency vascular intervention. The dosage would be similar to the pre-angioplasty dosage and would typically be completed by about four to twelve weeks after the angioplasty. Thus, the invention encompasses the treatment or prevention of restenosis in patients after surgical intervention by the administration of thalidomide or an analogue, metabolite or pro-drug thereof.

4.3.3 Coated Surgical Devices and Their Use in Surgery

In another embodiment, stent or other devices used in surgical procedures such as angioplasty are coated with thalidomide or another compound of the invention prior to use in the patient. This coating is designed to prevent restenosis and to otherwise benefit the patient. Systemic administration of thalidomide or another compound of the invention after surgical intervention is also contemplated. It should be recognized that multilayer coatings or releaseable coatings are also encompassed. Releaseable coatings can directly deposit the active compound e.g., thalidomide to the area at risk for restenosis. Alternatively, topical/internal applications can be used.

In such an embodiment, the compounds of the invention may be coated or sealed on a prosthetic device which is suitable, e.g., for implantation or other use in a subject, preferably a human. Examples of such devices include, but are not limited to, all types of angioplasty devices including a stent or stent/graft, or a commercial synthetic vascular graft or a biologic vascular graft. Any stent, stent/graft or tissue engineered vascular graft ("tubes") known in the art can be coated or sealed with the compounds of the present invention. The tubes can be metallic, or made from a biocompatible polymer, as well as a biodegradable polymer, such as, e.g., dacron polyester, poly(ethylene terephthalate), polycarbonate, polymethylmethacrylate, polypropylene, polyalkylene oxalates, polyvinylchloride, polyurethanes, polysiloxanes, nylons, poly(dimethyl siloxane), polycyanoacrylates, polyphosphazenes, poly(amino acids), ethylene glycol I dimethacrylate, poly(methyl methacrylate), poly(2-hydroxyethyl methacrylate), poly(HEMA), polyhydroxyalkanoates, polytetrafluorethylene, polycarbonate, poly(glycolide-lactide) co-polymer, polylactic acid, poly($\epsilon$-caprolactone), poly($\beta$-hydroxybutyrate), polydioxanone, poly($\gamma$-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups in which the polymers retain their structural integrity while allowing for attachment of molecules, such as proteins, nucleic acids, and the like. The tubes can also be fabric-coated metal structures. The tubes can also be made from combinations of metal and polymer. The tubes can be configured into any desired shape or conformation, such as, for example, linear, tapered, bifurcated, etc., and may be prepared using fiber technology, such as, e.g., crimped, woven, knitted, velour, double velour, with or without coils. The tubes can also be prepared by chemical extrusion, casting or molding using, for example, porous materials having linear or random pores that are circular or geometric in shape.

There are a variety of methods of manufacture available to provide a prosthetic device, coated on at least one surface with a sufficient amount of a compound of the present invention. The resulting coating is preferably uniform and should be integral so that contact between the device surface(s) and the surrounding tissue is precluded. The compounds can be applied to the device by spraying at least one surface of the device with the compounds in suspension, and allowing the applied surface to dry. In another embodiment, the device can be dipped into such a suspension, or by casting a suspension of the compounds over the device, or by layering a device the a suspension of the compounds over the device, or by impregnating a device with a suspension of the compounds. The compounds may be applied to the inside surface of a tube. By applying the compounds on the inside of the tube, the compounds promote proper reendothelialization of the lumen wall, promote wound healing and prevent or inhibit one or more cardiovascular disease states, such as stenosis, restenosis or intimal and neointimal hyperplasias.

The particular amount of the preparation to be applied to the device can be easily determined empirically by comparing devices with different amounts of the compound coated thereon and determining the efficacy of each by, for example, measuring. Also, one skilled in the relevant art and who is familiar with standard treatments would also be in a position to easily evaluate the efficacy of a device. Moreover, more than one coat of the compounds, either untreated or crosslinked, can be applied to a device. It is highly desirable to inspect the device once coated to insure that there are no gaps or breaks present in the coating.

Other methods of coating stents are well known in the art and are contemplated by the invention, for example, U.S. Pat. No. 5,637,113 describes coating stents with a polymer film, U.S. Pat. No. 5,837,313 describes a drug release stent coating process; both of these patents are incorporated herein in their entireties and for all purposes.

In a specific embodiment, a stent coated with the compounds the present invention, is provided. The compounds in or on the stent may be complexed with a drug, such as an antibiotic agent or an antiviral agent, or mixtures thereof, in order to insure against graft rejection. Additional drugs which may be added to the coating include antiplatelets, antithrombins, cytostatic and antiproliferative agents for example. Compounds such as thalidomide may not need protection against graft rejection since thalidomide may have this effect itself.

The methods used for implanting the coated devices are analogous to those used for the implantation of such devices without the coating, and, of course, depend on the nature of the condition to be modified or corrected. The surgery can be performed under either local or systemic anesthesia and, generally, involves an incision, spacing to accommodate the implant, insertion, and suture.

The following examples will serve to further typify the nature of this invention but should not be construed as a limitation in the scope thereof, which scope is defined solely by the appended claims.

5. WORKING EXAMPLES

5.1 Example

Tablets, each containing 50 mg of 1-oxo-2-(2,6-dioxo-piperidin-3yl)-4-amino-isoindoline can be prepared in the following manner:

| Constituents (for 1000 tablets) | |
|---|---|
| 1-oxo-2-(2,6-dioxo-piperidin-3yl)-4-amino-isoindoline | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

5.2 Coating of a Stent

A 5% (w/w) solution of silicone solid in tetrahydrofuran (THF) (HPLC grade, Aldrich or EM Science) is prepared by adding the required THF and a crosslinker agent into the silicone mixture. A separate 0.5% (w/w) solution of 1-oxo-2-(2,6-dioxo-piperidin-3yl)-4amino-isoindoline in THF is prepared by adding THF into a beaker containing 1-oxo-2-(2,6-dioxo-piperidin-3yl)-4amino-isoindoline. The ratio of $W_{drug}/W_{silicone\ solid}$ is 0.1. The coating of the stent in an expanded state is accomplished by spraying one cycle of silicone solution, waiting for a short period of time (about 30 seconds), and spraying one cycle of solution, waiting for a short period of time (about 30 seconds), and then repeating the spraying sequence. The very last spray cycle is silicone solution. For a coating thickness of 30 microns, about 30 cycles each is applied. The number of spray cycles used depends on the solution viscosity, the droplet size and the flow rate. The coated stent is then moved to a convection oven and cured at 150° C. for 45 minutes.

What is claimed is:

1. A method of treating atherosclerosis in a mammal comprising administering to a mammal having atherosclerosis an effective amount of 1,3-dioxo-2-(2,6-dioxopiperidin-3-yl) isoindoline substituted with amino in the benzo ring.

2. A method of treating atherosclerosis in a mammal comprising administering to a mammal having atherosclerosis an effective amount of 1,3-dioxo-2-(2,6-dioxopiperidin-3-yl)-4-aminoisoindoline having the formula,

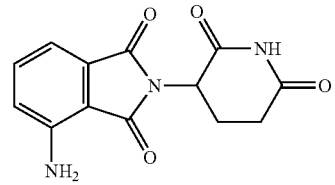

as a free base or a physiologically acceptable salt or an optically active enantiomer thereof.

3. The method of claim 1 or 2 wherein the atherosclerosis is in the aorta, coronary artery, mesenteric arteries, or carotid arteries.

4. The method of claim 1 or 2 wherein the atherosclerosis is in a renal artery.

5. The method of claim 1 or 2 wherein the mammal is a human.

6. The method of claim 1 or 2 wherein approximately 0.01 mg/kg to 300 mg/kg of body weight is administered per day.

7. The method of claim 1 or 2 wherein the administration is oral.

8. The method of claim 1 or 2 wherein the atherosclerosis is in the common iliac arteries, internal iliac arteries, external iliac arteries, or the pulmonary arteries.

9. The method of claim 1 or 2, wherein the compound is administered in the form of a capsule, a tablet, a cachet, a solution, a suspension, an emulsion, a granule, a powder or a bolus.

10. The method of claim 2, wherein the compound is 1,3-dioxo-2-(2,6-dioxopiperidin-3-yl)-4-aminoisoindoline free base.

11. The method of claim 2, wherein the compound is a physiologically acceptable salt of 1,3-dioxo-2-(2,6-dioxopiperidin-3-yl)-4-aminoisoindoline.

12. The method of claim 2, wherein the compound is an optically active enantiomer.

13. The method of claim 12, wherein the optically active enantiomer is R enantiomer.

14. The method of claim 12, wherein the optically active enantiomer is S enantiomer.

* * * * *